(12) United States Patent
Kurtz

(10) Patent No.: US 10,449,325 B2
(45) Date of Patent: Oct. 22, 2019

(54) POSITIVE AIRWAY PRESSURE RESPIRATION MASK

(71) Applicant: Rainbow Vista Medical Devices Incorporated, Gresham, OR (US)

(72) Inventor: Kenneth Marcus Kurtz, Gresham, OR (US)

(73) Assignee: Rainbow Vista Medical Devices, Inc., Gresham, OR (US)

( * ) Notice: Subject to any disclaimer, the term of this patent is extended or adjusted under 35 U.S.C. 154(b) by 239 days.

(21) Appl. No.: 15/468,427

(22) Filed: Mar. 24, 2017

(65) Prior Publication Data

US 2017/0274169 A1 Sep. 28, 2017

Related U.S. Application Data

(60) Provisional application No. 62/312,841, filed on Mar. 24, 2016.

(51) Int. Cl.
*A61M 16/20* (2006.01)
*A61M 16/06* (2006.01)
(52) U.S. Cl.
CPC ...... *A61M 16/208* (2013.01); *A61M 16/0616* (2014.02); *A61M 16/0683* (2013.01)
(58) Field of Classification Search
CPC ............ A61M 16/208; A61M 16/0616; A61M 16/0683; A61M 16/209; A61M 15/002
See application file for complete search history.

(56) References Cited

U.S. PATENT DOCUMENTS

| | | | |
|---|---|---|---|
| 4,549,543 A | 10/1985 | Moon | |
| 4,960,121 A | 10/1990 | Nelson et al. | |
| 6,435,184 B1 | 8/2002 | Ho | |
| 6,513,526 B2 | 2/2003 | Kwok et al. | |
| 7,861,715 B2 | 1/2011 | Jones et al. | |
| 8,109,271 B2 | 2/2012 | Vandine | |
| 8,365,734 B1 | 2/2013 | Lehman | |
| 8,490,623 B2 | 7/2013 | Berthon-Jones et al. | |
| 8,505,536 B2 | 8/2013 | Kielow et al. | |
| 8,522,785 B2 | 9/2013 | Berthon-Jones et al. | |
| 8,550,084 B2 | 10/2013 | Ng et al. | |
| 8,695,602 B2 | 4/2014 | Pierro et al. | |
| 8,950,404 B2 | 2/2015 | Formica et al. | |

(Continued)

*Primary Examiner* — Bradley J Osinski
(74) *Attorney, Agent, or Firm* — Richards Patent Law, P.C.

(57) ABSTRACT

A nasal respiratory mask system configured to be placed on a user's face to provide respiratory gas under positive pressure to the user, the nasal respiratory mask system includes: a nasal mask shell configured to cover a user's nose and mouth, the nasal mask shell includes a first valve opening and a second valve opening, wherein the first valve opening is configured to receive a respiratory tube connected to a positive gas pressure source, wherein the second valve opening is configured to enable the entrance of fresh air when the pressure within the nasal mask shell cavity falls below a threshold pressure; and a securing system configured to secure the nasal mask shell to the user's face, wherein the securing system includes at least one horizontal securing strap, wherein the horizontal securing strap extends from a first side face of the nasal mask shell to a second side face of the nasal mask.

12 Claims, 10 Drawing Sheets

(56) References Cited

U.S. PATENT DOCUMENTS

| | | | |
|---|---|---|---|
| 2005/0098183 A1* | 5/2005 | Nash | A61M 16/06 128/206.21 |
| 2006/0201514 A1* | 9/2006 | Jones | A61M 16/06 128/206.21 |
| 2010/0170513 A1* | 7/2010 | Bowditch | A61M 16/00 128/204.23 |
| 2011/0265796 A1* | 11/2011 | Amarasinghe | A61M 16/06 128/206.28 |
| 2012/0289838 A1* | 11/2012 | Varga | A61B 5/0836 600/473 |
| 2013/0074845 A1 | 3/2013 | Smith et al. | |
| 2014/0069428 A1* | 3/2014 | Sears | F16K 5/0407 128/204.21 |
| 2014/0096774 A1 | 4/2014 | Olsen et al. | |
| 2014/0144445 A1 | 5/2014 | Bowditch et al. | |
| 2015/0083137 A1 | 3/2015 | Mittelstadt | |
| 2016/0263338 A1* | 9/2016 | Borsari | A61M 16/0463 |

* cited by examiner

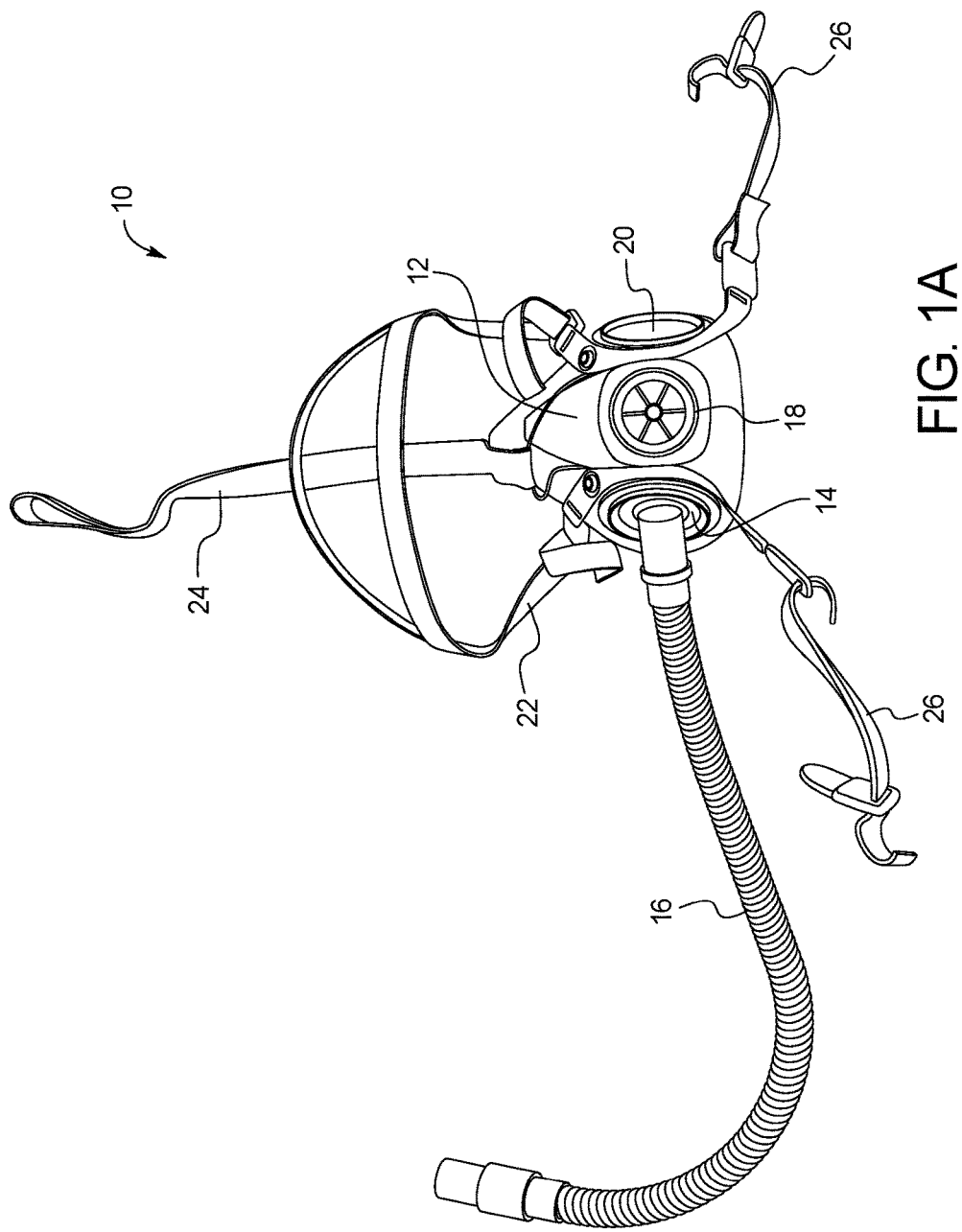

POSITIVE AIRWAY PRESSURE RESPIRATION MASK

BACKGROUND OF THE INVENTION

The present subject matter relates generally to a respiratory facemask. More specifically, the present invention relates to respiratory facemask that may be pressurized and worn during sleep to reduce the effects of central sleep apnea.

Central sleep apnea is a disorder that causes repeated cessation of breathing during sleep. For individuals suffering from central sleep apnea, the condition may cause discomfort during sleep, such as abruptly waking up with shortness of breath, mood changes, insomnia, headaches and snoring. One treatment option for central apnea is called continuous positive airway pressure (CPAP). This method involves wearing a mask over the nose during sleep, with the mask being attached a pump that supplies a continuous amount of pressurized air. This acts to hold open the upper airway, which may cause central apnea when closed.

Wearing masks during sleep, however, may cause difficulties for the user, especially when it comes to comfort for the user. Additionally, if the user moves around in certain positions, the mask may come off. Most importantly, wearing certain conventional respiratory facemasks has been known to cause suffocation if the pump providing the positive air pressure stops working and the user does not realize they are not getting air from the pump and the mask is sealed to the user's face.

Accordingly, there is a need for positive airway pressure respiration mask that provides a secure fit to the face, is comfortable to sleep with, and provides a mechanism to prevent suffocation in the event the positive air pressure fails, as described herein.

BRIEF SUMMARY OF THE INVENTION

To meet the needs described above and others, the present disclosure provides a nasal respiration mask system that provides a secure fit to the face, is comfortable to sleep with, and minimizes the risk of blockage and suffocation.

A nasal respiratory mask system configured to be placed on a user's face to provide respiratory gas under positive pressure to the user, the nasal respiratory mask system includes: a nasal mask shell configured to cover a user's nose and mouth, the nasal mask shell includes a first valve opening and a second valve opening, wherein the first valve opening is configured to receive a respiratory tube connected to a positive gas pressure source, wherein the second valve opening is configured to enable the entrance of fresh air when the pressure within the nasal mask shell cavity falls below a threshold pressure; and a securing system configured to secure the nasal mask shell to the user's face, wherein the securing system includes at least one horizontal securing strap, wherein the horizontal securing strap extends from a first side face of the nasal mask shell to a second side face of the nasal mask.

An advantage of the present device includes correcting higher outflow exhaust pressures associated with conventional masks. The present device is designed to operate at optimal exhaust rates and zero leak rates.

An advantage of the present device is that it provides a tight seal to the face but applies less pressure to the face than conventional models.

Another advantage of the present device is that the mask deforms rather than remaining rigid, thereby making the mask suitable for back, side and stomach sleepers.

A further advantage of the present device is that it may be fully disassembled and cleaned. It may also withstand the heat of blow dryers or machine dryers.

Yet another advantage of the present device is that it may have a low leak rate due to its optimal seal.

A further advantage of the present device is the incorporation of a safety valve positioned between a first end and second end of the respiratory tube, such that if the positive pressure from the air pump decreases, the safety valve allows fresh air to enter into the respiratory tube leading to the nasal face mask to prevent suffocation.

Additional objects, advantages and novel features of the examples will be set forth in part in the description which follows, and in part will become apparent to those skilled in the art upon examination of the following description and the accompanying drawings or may be learned by production or operation of the examples. The objects and advantages of the concepts may be realized and attained by means of the methodologies, instrumentalities and combinations particularly pointed out in the appended claims.

BRIEF DESCRIPTION OF THE DRAWINGS

The drawing figures depict one or more implementations in accord with the present concepts, by way of example only, not by way of limitations. In the figures, like reference numerals refer to the same or similar elements.

FIG. 1A is a top perspective view of an embodiment of the disclosed mask.

FIG. 6A is an embodiment of a safety valve, wherein the positive pressure from the air pump is greater than 2 mm Hg.

It should be noted that various changes and modifications to the presently preferred embodiments described herein will be apparent to those skilled in the art. Such changes and modifications may be made without departing from the spirit and scope of the present invention and without diminishing its attendant advantages.

DETAILED DESCRIPTION OF THE INVENTION

By providing a lightweight and flexible mask that conforms to the face with a secure seal, the disclosed mask achieves both comfort, safety, and effectiveness. The close fit on the face and flexible construction enables the mask to deform rather than getting pulled from the face like more rigid models. Additionally, the unique harness design increases the comfort and adjustability of the system.

Figure 1B:
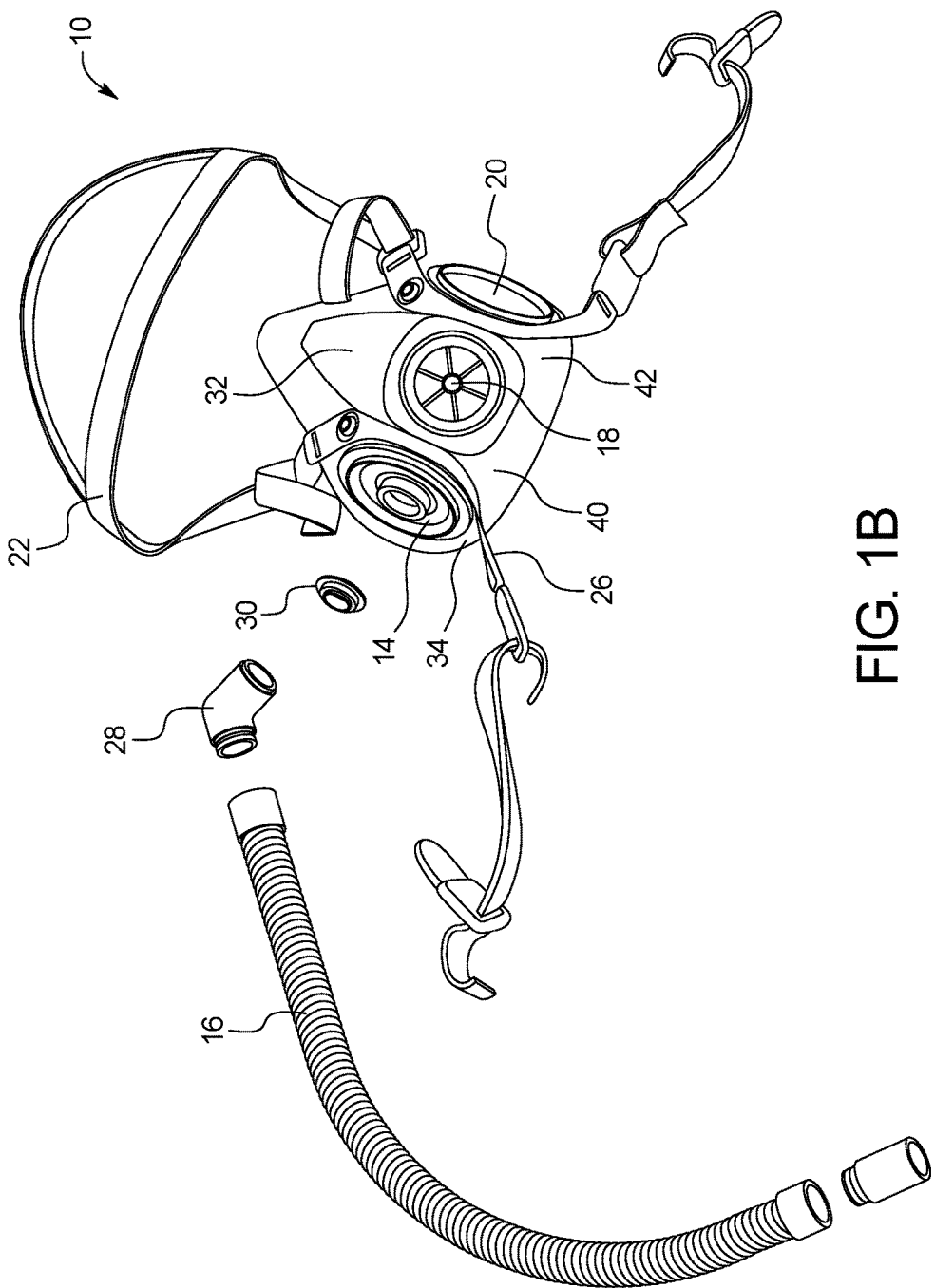
FIG. 1B is an exploded view of an embodiment of the disclosed inlet hose and the mask.
Figure 1C:
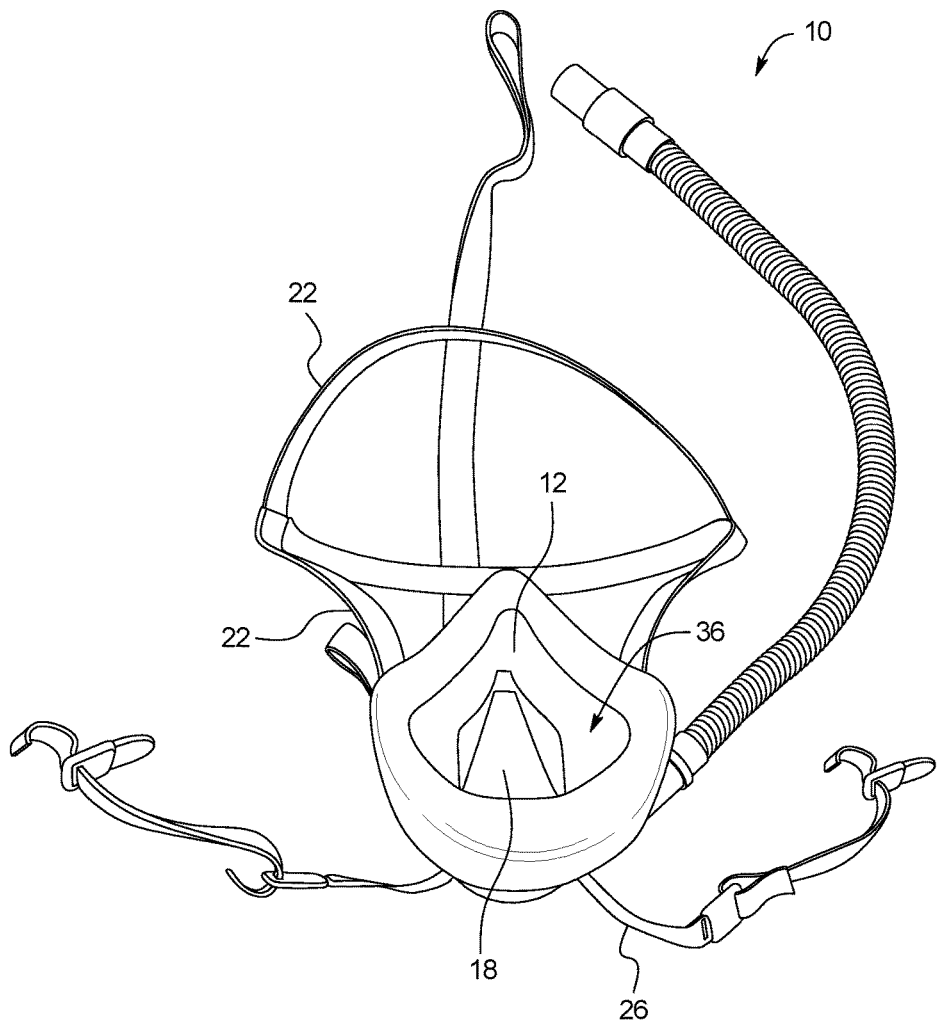
FIG. 1C is a bottom perspective view of an embodiment of the mask.

As shown in FIGS. 1A-1C, the disclosed nasal respiratory mask system 10 includes a nasal mask shell 12, a first opening valve 14 configured to receive a respiratory tube 16 connected to a positive gas pressure source, a second opening valve 18 configured to function as a anti-suffocation valve, and a securing system configured to secure the nasal mask shell to a user's face.

The first opening valve 14 may be positioned on a side face 34 of the nasal mask shell 12, and the second opening valve 18 (i.e., anti-suffocation valve) may be positioned on a center front side face 32 of the nasal mask shell 12. The second valve opening 18 is configured to enable the entrance of fresh air when the pressure within the nasal mask shell cavity 36 falls below a threshold pressure. The nasal mask shell 12 may also include an exhaust valve 20, wherein the exhaust valve 20 may be positioned on a side face of the nasal mask shell 12.

The second opening valve 18 can be double layered to eliminate leaks under pressure. The function and placement of the second opening valve 18 is to supply additional air if the user suddenly gasps for air (crisis breathing) and/or supply air when the machine/pump is off. If there is any positive pressure in the mask, the second opening valve is closed. The second opening valve 18 opens to fresh air (due to mechanical flexibility of the rubber disks) only if the machine/pump is off (i.e., zero pressure) or the user gasps at a pressure higher than the machine is supplying. In an example, the nasal respiratory mask system 10 may also include a pressure sensor such that when the detected pressure in the nasal mask cavity 36 is less than a selected threshold pressure (e.g., less than 15 mm Hg, less than 10 mm Hg, or less than 6 mm Hg), the second opening valve 18 opens to allow fresh air to enter into the nasal mask shell cavity 36. Such mechanism may guarantee that fresh air will pass through the mask even if the pumping machine has stopped providing air for some reason, thereby preventing suffocation of the user. Specifically, by providing the anti-suffocation valve, users may avoid air deprivation episodes that cause them to be awakened during sleep. Additionally, the position of the second opening valve 18 on the center front face side, the second opening valve 18 is difficult to block due to its size and central placement. Further, even if the nasal mask shell is pushed inward, the second opening valve 18 may open rather than become blocked, further preventing suffocation.

The second opening valve 18 may include a filter that allows for fresh air to enter. Alternatively, or in addition, the anti-suffocation valve may be open to function as a drink port, with openings in the second opening valve 18 that may accommodate a straw that the users may drink liquids through.

Figure 2:
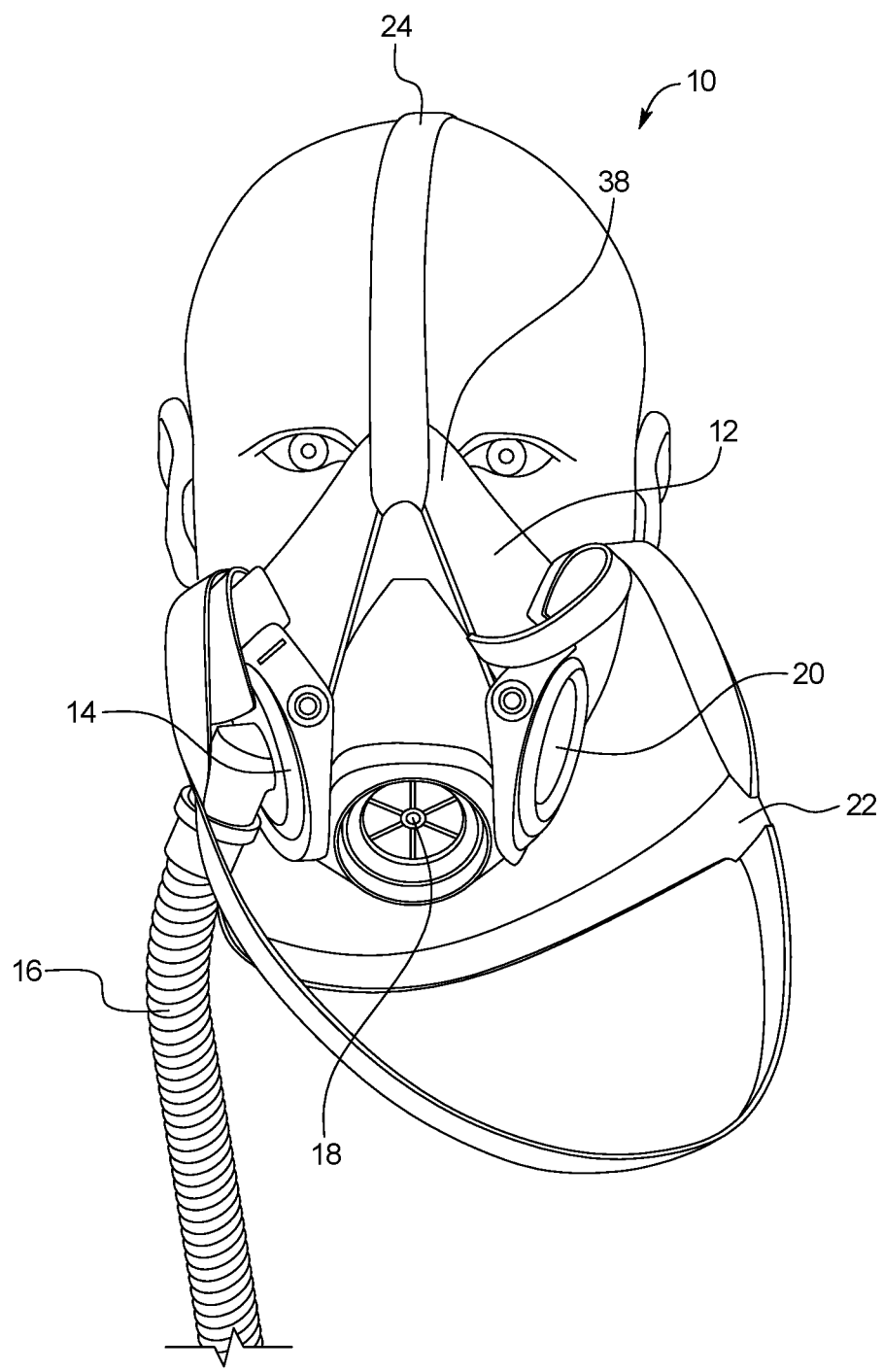
FIG. 2 is a view of the mask worn on a user wherein the vertical securing strap is in place, wherein the horizontal securing strap has not been secured to a user's head.
Figure 3:
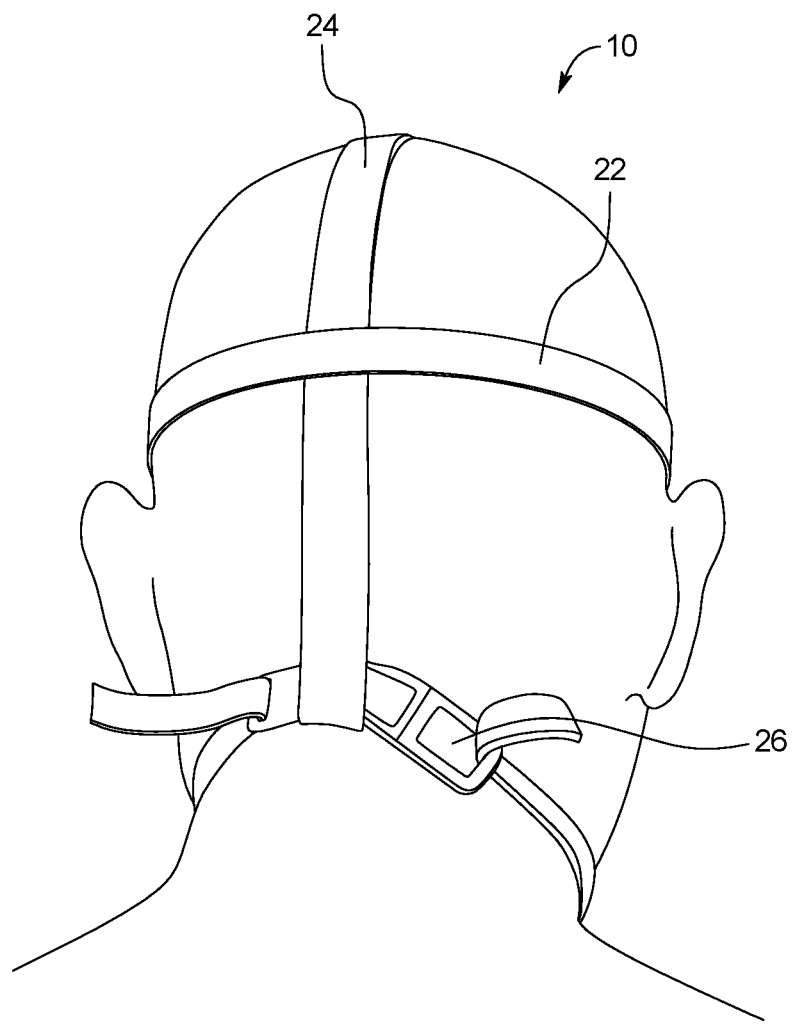
FIG. 3 is a back view of an embodiment the mask secured to a user's head.
Figure 4:
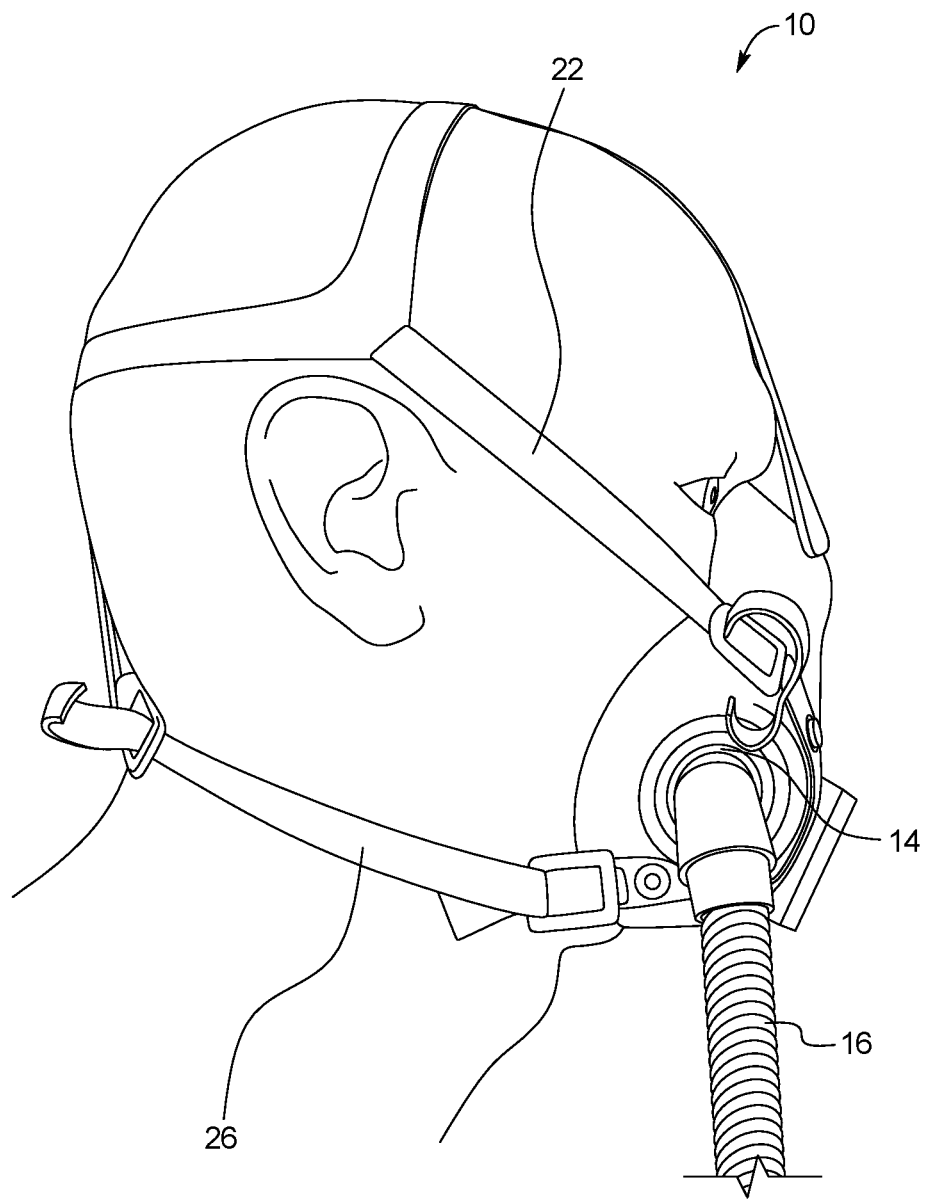
FIG. 4 is a side view of an embodiment of the mask secured to a user's head.

As shown in FIGS. 2-4, the securing system may connect to the nasal mask shell 12 from two to five points or areas on the nasal mask shell 12. The securing system may include at least one horizontal securing strap 22, wherein the horizontal securing strap 22 extends from a first side face of the nasal mask shell 12 to a second side face of the nasal mask shell 12. The securing system may include a vertical securing strap 24, wherein when the nasal mask system is placed on the user, the vertical securing strap 24 can extend from a top side face 38 of the nasal mask shell 12 to a portion of the horizontal securing strap 22 positioned on the backside of a user's head. The nasal respiratory mask system can further include a chin strap 26 extending from a first bottom side face of the nasal mask shell 12 to a second bottom side face of the nasal mask shell 12, wherein when the nasal mask system 10 is placed on a user, the vertical securing strap 24 extends from a top side face of the nasal mask shell 12 to a portion of the chin strap 26 positioned at the base of a user's neck, as shown in FIG. 3.

The horizontal securing strap 22 may split into two straps wherein when in use on a user a first branch is positioned above the crown of the head of the user and the second branch is positioned below the crown of the head of the user, as shown in FIG. 4.

In other words, the vertical securing strap 24 may extend from the bridge of the nose of the nasal mask shell over the crown of the user's head and to the horizontal strap 22 positioned near the crown of the head of the user, and/or may connect to the chin strap positioned at the nape of the neck and looping around a horizontal strap 22 or a chin strap 26.

The vertical securing strap 24 and the horizontal securing strap 22 may be available in a variety of sizes. Alternatively, or in addition to, the vertical securing strap 24 and the horizontal securing strap 22 may be adjustable. In addition, a fabric tape can be applied to the one or both of the vertical and horizontal securing strap to protect the skin of the wearer, to prevent dermatitis.

The chin strap 26 may be composed of one or two separate straps that extend from a first bottom side face 40 to a second bottom side face 42 of the chin component of the nasal mask shell 12 around the back of the head, meeting in the middle at the nape of the neck. These two straps comprising the chin strap 26 may be connected with a clasp. By releasing the clasp (which may be accomplished using only one hand), the user may remove the mask. The chin straps 26 may be adjustable for the user's comfort. The chin straps 26 may also act to keep the jaw in position. This may help to stabilize the pressure by keeping the mouth from opening too much. If the mouth opens slightly during sleep, the pressure change will not cause wake-up. Further, a beard guard (inlet protection device) inside the nasal mask shell 12 can be incorporated to guard the inlet opening if the user has a heavy beard or facial feature that can possibly clog or block the first opening valve.

The straps of the securing system may provide varying elasticities and length adjustments to optimize user comfort.

The nasal respiratory mask system 10 may include an exhaust valve 20 to further prevent blockages. The exhaust valve can include a fabric patch in the valve, wherein the fabric patch extends over the opening of the valve and includes a perforated fabric. The perforated fabric can be applied to the valve via double-sided tape (inside and/or outside the mask). In addition, the present design prevents the air flowing from the exhaust valve from forcibly contacting the user or a partner sleeping next to the user. The exhaust valve 20 may be positioned on a side face of the mask where there is less leverage, making it harder to pull off compared to conventional mask models that place the exhaust valve in the center of the mask.

The first opening valve 14 may be on either the left or right side of the mask. The side positioning of the first opening valve 14 adapted to receive an inlet respiratory hose 16 will allow air to blow in from the side and gently onto the cheek, instead of directly up the nose or into the mouth, which may increase comfort during use of the nasal respiratory mask system 10.

The respiratory tube 16 can connect directly to the first opening valve 14. Alternatively, or in addition to, as shown in FIG. 1B, the respiratory tube 16 can connect to the first opening valve 14 via a junction 28, wherein an O-ring 30 is used to further secure the seal from the respiratory tube 16 to the first opening valve 14 to prevent gas leaks. The junction 28 can be an elbow junction, which may facilitate a direct flow of air into the nasal mask shell 12, and prevent the respiratory tube from being bent and preventing air flow. The respiratory tube 16 connects the first opening valve 14 to an air pump for supplying positive pressure to the nasal mask shell 12. In an example, the respiratory tube 16 can be between 1800 and 1900 mm, for example 1850 mm, which provides a volume of the hose for optimal function and safety.

Figure 5:
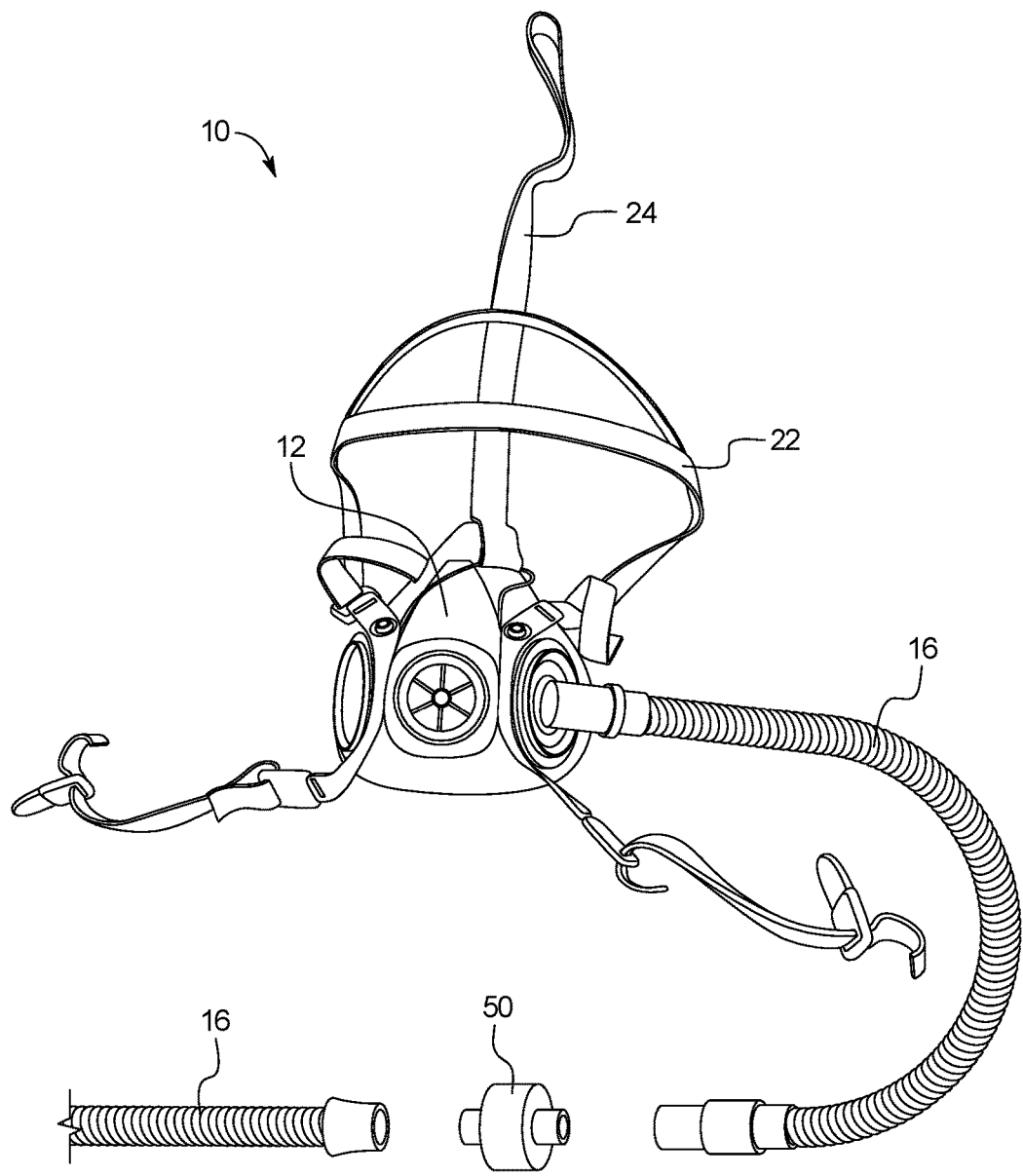
FIG. 5 is an exploded view of an embodiment of the disclosed mask including a safety valve positioned within the respiratory tube.
Figure 6A:
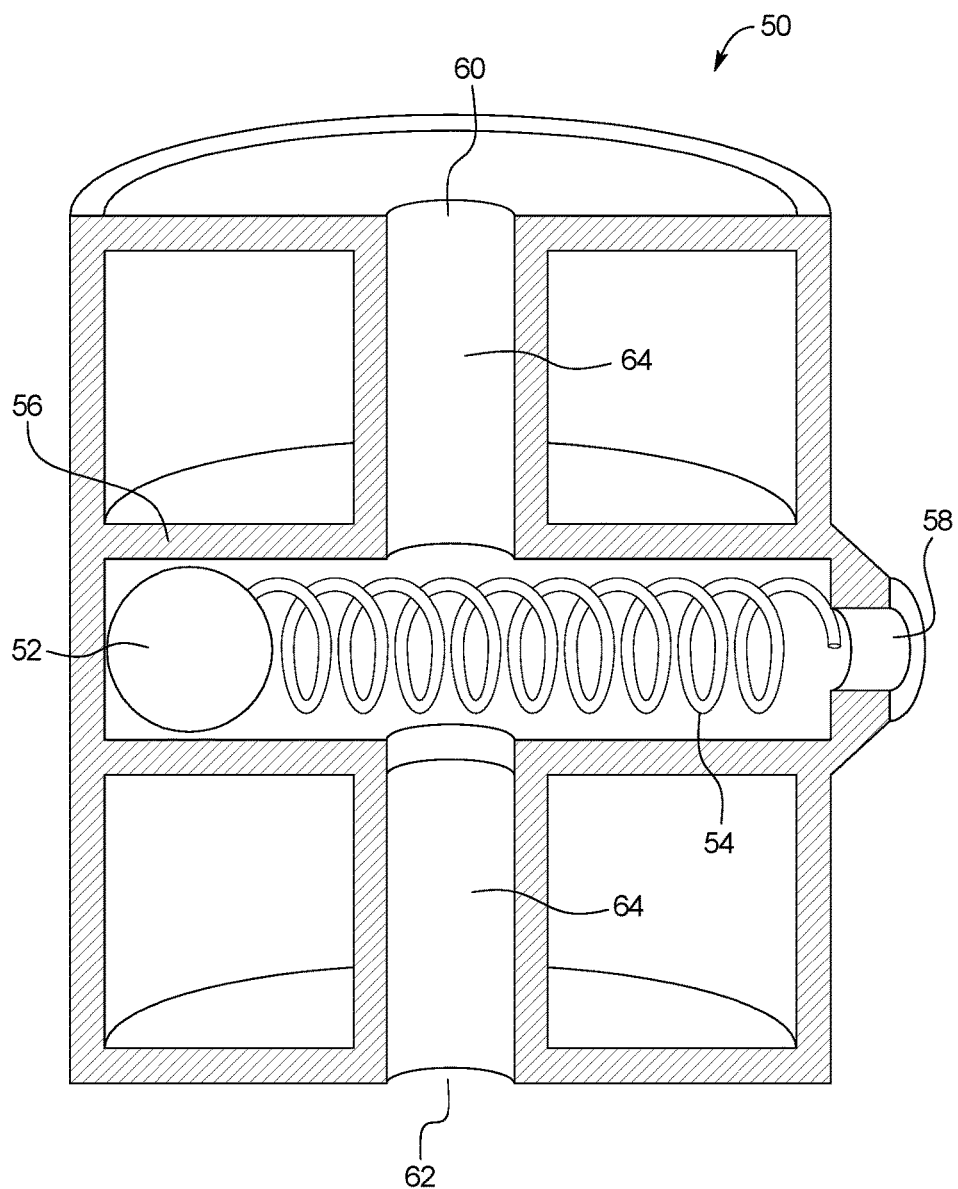
FIG. 6A is an embodiment of a safety valve, wherein the positive pressure from the air pump is less than 2 mm Hg.
Figure 6B:
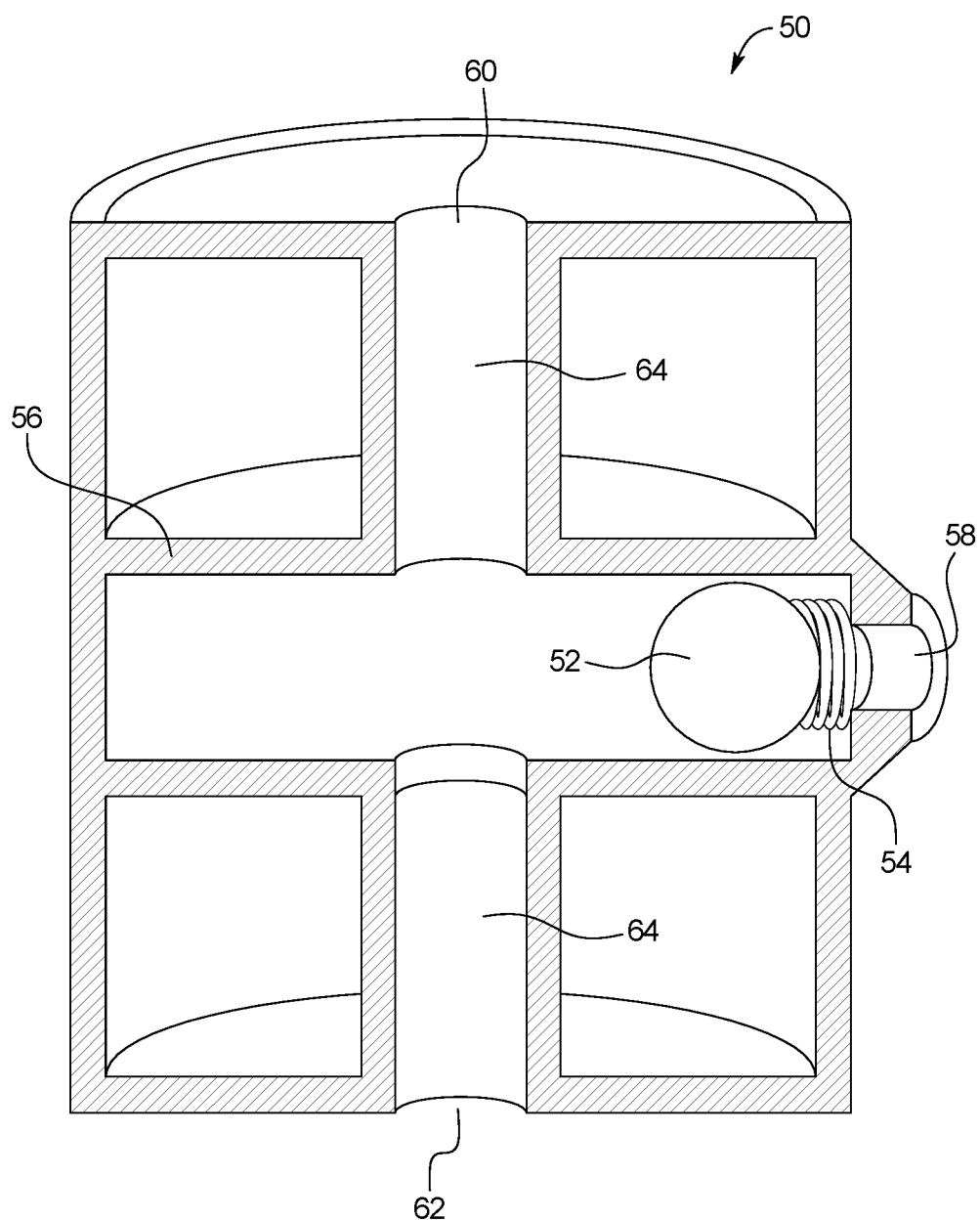

As shown in FIG. 5, a safety valve 50 can be positioned within the respiratory tube 16, wherein the safety valve 50 is positioned along the respiratory tube 16 between the first opening valve 14 and the air pump. The safety valve is light in weight and does not contribute to a significant increase in sound during operation. In an example, the safety valve is positioned at the end of the respiratory tube 16 and the air pump (i.e., between the respiratory tube 16 and the air pump). As shown in FIGS. 6A-6B, the safety valve 50 includes an inner tube housing a spherical member 52 and a compressible spring 54. The inner tube 56 is perpendicular to an air flow tube 64 wherein the air flow from the air pump (e.g., positive gas pressure source) passes through the air flow tube 64 from a first end 60 and second end 62 of the safety valve 50. The first end and second end can connect to two sections of the respiratory tube 16, or wherein the first end attaches to the respiratory tube 16 and the second end attaches to the air pump. The safety valve 50 also includes a fresh air opening 58 that extends from the inner tube 56 to the outer surface of the safety valve exposed to fresh air. As shown in FIG. 6A, when the pressure is less than 2 mm Hg (i.e., the air pump is not supplying positive pressure through the respiratory tube), the spring is depressed such that the spherical member does not block a fresh air opening. In other words, when the pressure is less than 2 mm Hg, the spring is depressed, removing the spherical member from the opening to allow fresh air to enter the respiratory tube and flow to the nasal mask to prevent suffocation. In contrast, as shown in FIG. 6B, when the pressure is greater than 2 mm Hg (the air pump is supplying positive pressure through the respiratory tube) the forced air causes the spring 54 to be compressed, thereby pushing the spherical member 52 to block the fresh air opening 58.

The safety valve 50 can be a backflow valve, wherein the backflow valve is closed to fresh air when the machine/pump is on and it is open to fresh air when the machine/pump is off. The backflow valve is protected by a circular filter medium such that the user is protected from dust when the machine/pump is off. For safety, the backflow valve is designed such that the user can breathe normally if the machine is off and not supplying air (i.e., preventing suffocation).

Figure 7A:
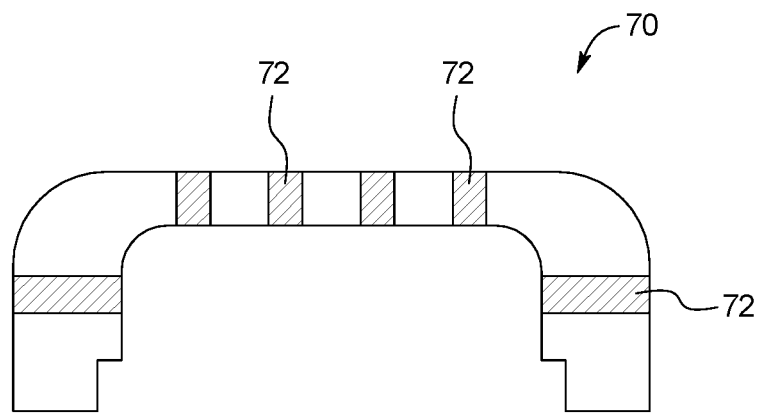
FIG. 7A is a cross sectional view of an embodiment of a beard guard.
Figure 7B:
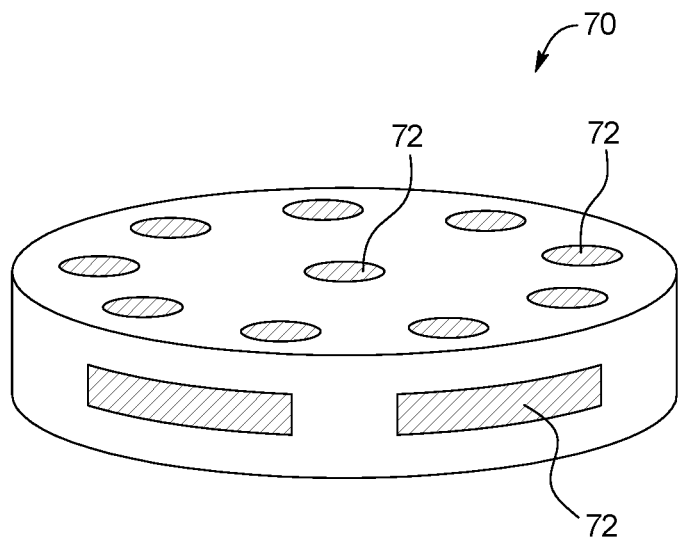
FIG. 7B is a top perspective view of an embodiment of a beard guard 70.

FIGS. 7A-7B depicts an embodiment of a beard guard 70. FIG. 7A is a cross section of the beard guard depicting the perforations 72 to allow air to enter the beard guard 70. FIG. 7B is a top perspective view of the beard guard 70. The perforations can be any suitable size to allow air to enter inside the beard guard. The beard guard can also include slits to allow in air into the beard guard.

The nasal respiratory mask system 10 may also include an outlet valve for fluids or other failure issues. The mask may be easily lifted from the face in case of emergency to eject undesirable matter like bodily fluids or stray hair, and also allows the user to scratch under the mask. The mask may be returned to its original position without the need to remove the mask.

The nasal mask shell 12 may include a lightweight, flexible construction that allows the structure to be deformed and bend at the application of external pressure, in contrast to the conventional rigid structure. The nasal mask shell 12 may also come in a variety of sizes to accommodate the needs of the user. The interior edge of the nasal mask shell 12 may include a rim of cushion for comfort and provide a secure seal to a user's face. Further, a broad chin seal area on the face piece may help to circumscribe facial hair and provide a better seal. The optional chin seal can be broadened, narrowed, adjusted, or customized for a particular user.

The volume of the nasal mask shell and external placement of the exhaust valve 20 may cause re-breathing of carbon dioxide trapped in the mask dead space, which may help to reduce central apnea. The design of the nasal respiratory mask system 10 includes comparatively high volume in the nasal mask shell 12 and an external tuned exhaust valve 20, with a comparatively tight seal. A curved seal edge of the nasal mask shell may increase dead space in the mask, but not mask weight or size, so it maximizes mask volume while minimizing mask size.

The nasal respiratory mask system may be made according to OSHA specifications and may be worn for 8 hours or more per day. Additionally, it may be chemical resistant to prevent skin oils, creams, ointments, etc. from adhering to the system.

The nasal respiratory mask system may be used at normal CPAP machine pressures. The pressure can be adjusted to ensure a reliable and comfortable seal between the mask and the user. For example, the pressure of can be up to about 12 mm Hg, up to 25 mm Hg, up to 40 mm Hg, or up to 45 mm Hg.

The nasal respiratory mask system may be worn with a ski mask at higher pressures to help seal under the eyes. It may also be worn with a nose strip or other breathing aids, such as a dental appliance or nasal insert.

Yet another advantage of the nasal respiratory mask system is that it does not require a humidifier because an appropriate humidity level is better retained in the mask compared to other masks. The moist, heated air remains in the mask shell. This may reduce machine/system costs overall because a humidifier is not required. Without a humidifier, the present system may be run for relatively longer periods of time on a battery. It also travels more easily. If weight and size and lack of electrical utilities are an issue, the present system may be used 'in the field' with a battery. For the performance, the machine has the advantage of being lightweight and portable.

Another advantage of the present system is that it may not require pressure relief features (i.e., machine algorithmic pressure adjustments for comfort). The nasal respiratory mask system takes time to pressurize and de-pressurize due to its volume and flexibility, so pressure-relief comfort is built in to the design. Additional pressure relief may be achieved using the nasal respiratory mask system with existing comfort algorithms. Because pressure relief isn't required, the present system costs may be decreased.

A further advantage of the invention is that the nasal respiratory mask system may be produced inexpensively of durable materials.

Another advantage is the nasal mask shell may be trimmed with a sharp scissors along the chin edge to allow the mask to sit closer the face and seal better.

Acknowledging that all CPAP masks may cause facial indentations from use, the present system is advantageous in that the depth and placement of the indentations may be in places that are physically more comfortable and attractive than other masks.

Acknowledging that all CPAP masks may cause dermatitis, an advantage of the present system is that any thin cotton handkerchief, bandana, or cap may be worn under the headgear to reduce the dermatitis. In addition, fabric tape can be used with the headgear to reduce dermatitis.

It should be noted that various changes and modifications to the embodiments described herein will be apparent to those skilled in the art. Such changes and modifications may be made without departing from the spirit and scope of the present invention and without diminishing its attendant advantages. For example, various embodiments of the systems and methods may be provided based on various combinations of the features and functions from the subject matter provided herein.

I claim:

1. A nasal respiratory mask system configured to be placed on a user's face to provide respiratory gas under positive pressure to the user, the nasal respiratory mask system comprising:
   a nasal mask shell configured to cover a user's nose and mouth, the nasal mask shell includes a first valve opening and a second valve opening, wherein the first valve opening is configured to receive a respiratory tube connected to a positive gas pressure source, wherein the second valve opening is configured to enable the entrance of fresh air when the pressure within the nasal mask shell cavity falls below a threshold pressure;
   a securing system configured to secure the nasal mask shell to the user's face, wherein the securing system includes at least one horizontal securing strap, wherein the horizontal securing strap extends from a first side face of the nasal mask shell to a second side face of the nasal mask; and
   a respiratory tube, wherein a first end of the respiratory tube is removeably connected to the first valve opening in the nasal mask shell, wherein a second end of the respiratory tube is configured to attach to a first end of a safety valve, wherein a second end of the safety valve is connected to a positive gas pressure source, wherein air from the positive gas pressure source flows through an air flow tube extending from the second end of the safety valve to the first end of the safety valve,
   wherein an inner tube extends perpendicular from the air flow tube to a fresh air opening within a surface of the safety valve, wherein the inner tube houses a spring and a spherical member.

2. The nasal respiratory mask system of claim 1 further comprising a respiratory tube, wherein a first end of the respiratory tube is removeably connected to the first valve opening in the nasal mask shell, wherein a second end of the respiratory tube is configured to connect to a positive gas pressure source.

3. The nasal respiratory mask system of claim 1 wherein the securing system further includes a chin strap extending from a first bottom side face of the nasal mask shell to a second bottom side face of the nasal mask shell, wherein when the nasal mask system is placed on a user, a portion of the chin strap is positioned at the base of a user's neck.

4. The nasal respiratory mask system of claim 1 wherein the securing system includes a vertical securing strap, wherein when the nasal mask system is placed on the user, the vertical securing strap extends from a top side face of the nasal mask shell to a portion of the horizontal securing strap positioned on the backside of a user's head.

5. The nasal respiratory mask system of claim 4 wherein the nasal respiratory mask system further includes a chin strap extending from a first bottom side face of the nasal mask shell to a second bottom side face of the nasal mask shell, wherein when the nasal mask system is placed on a user, the vertical securing strap extends from a top side face of the nasal mask shell to a portion of the chin strap positioned at the base of a user's neck.

6. The nasal respiratory mask system of claim 1 further comprising an exhaust valve, wherein the exhaust valve is configured to enable the exit of excess of air from the nasal mask shell cavity.

7. The nasal respiratory mask system of claim 1 further comprising a pressure sensor to determine a detected pressure within the nasal mask shell cavity, wherein when the detected pressure is below a threshold pressure, the second opening valve opens allowing the entrance of air through the second opening valve.

8. The nasal respiratory mask system of claim 1 wherein the first opening valve is positioned on a side face of the nasal mask shell.

9. The nasal respiratory mask system of claim 1 wherein the second opening valve is positioned on a front side face of the nasal mask shell.

10. The nasal respiratory mask system of claim 1 wherein upon the nasal mask shell receiving positive external pressure, the second opening valve opens enabling air to enter the nasal mask shell cavity.

11. The nasal respiratory mask system of claim 1, wherein if the air pressure within the air flow tube is less than 2 mm Hg, the spring is depressed and the fresh air opening is unimpeded by the spherical member thereby allowing fresh air to enter the inner tube and air flow tube.

12. The nasal respiratory mask system of claim 1, wherein if the air pressure within the air flow tube is greater than 2 mm Hg, the spring is compressed and the spherical member blocks the fresh air opening.

* * * * *